(12) United States Patent
Ichikawa et al.

(10) Patent No.: US 10,285,628 B2
(45) Date of Patent: May 14, 2019

(54) METHOD FOR DETECTING AMBULATORY STATUS AND DEVICE FOR DETECTING AMBULATORY STATUS

(71) Applicants: MicroStone Corporation, Kitasaku-gun, Nagano (JP); Akira Ichikawa, Saku-shi, Nagano (JP)

(72) Inventors: Akira Ichikawa, Saku (JP); Norihiko Shiratori, Saku (JP); Shigeya Okada, Saku (JP); Hidetaka Nozawa, Saku (JP)

(73) Assignees: MICROSTONE CORPORATION, Kitasaku-Gun, Nagano (JP); Akira Ichikawa, Saku-shi, Nagano (JP)

( * ) Notice: Subject to any disclaimer, the term of this patent is extended or adjusted under 35 U.S.C. 154(b) by 188 days.

(21) Appl. No.: 15/117,939

(22) PCT Filed: Feb. 27, 2015

(86) PCT No.: PCT/JP2015/055928
§ 371 (c)(1),
(2) Date: Aug. 10, 2016

(87) PCT Pub. No.: WO2015/129883
PCT Pub. Date: Sep. 3, 2015

(65) Prior Publication Data
US 2016/0345870 A1 Dec. 1, 2016

(30) Foreign Application Priority Data
Feb. 28, 2014 (JP) .................................. 2014-039341

(51) Int. Cl.
*A61B 5/00* (2006.01)
*A61B 5/11* (2006.01)

(52) U.S. Cl.
CPC .......... *A61B 5/1127* (2013.01); *A61B 5/0024* (2013.01); *A61B 5/0077* (2013.01);
(Continued)

(58) Field of Classification Search
CPC ..... A61B 5/112; A61B 5/1121; A61B 5/1122; A61B 5/1123; A61B 5/1124;
(Continued)

(56) References Cited

U.S. PATENT DOCUMENTS 5,146,929 A 9/1992 Sawhill
2009/0030345 A1 1/2009 Bonnet et al.
(Continued)

FOREIGN PATENT DOCUMENTS

JP 2008-307207 A 12/2008
JP 2009-106377 A 5/2009
(Continued)

OTHER PUBLICATIONS

Crosbie et al. "Patterns of spinal motion during walking", Gait & Posture vol. 5, Issue 1, 1997, pp. 6-12.*
(Continued)

*Primary Examiner* — Devin B Henson
(74) *Attorney, Agent, or Firm* — Birch, Stewart, Kolasch & Birch, LLP

(57) ABSTRACT

A method and a device with which an ambulatory status, including movements of an upper body, can be detected easily, without a complex operation of the equipment used, in a medical facility for rehabilitation or the like. In case of detecting the ambulatory status of a subject, the problem is solved by detecting the ambulatory status of the subject by measuring conditions of movement in at least two places, specifically, a lumber area and a thoracodorsal area of the subject.

1 Claim, 16 Drawing Sheets

(52) U.S. Cl.
CPC ............ *A61B 5/112* (2013.01); *A61B 5/1123* (2013.01); *A61B 5/6814* (2013.01); *A61B 5/6823* (2013.01); *A61B 5/6828* (2013.01); *A61B 5/725* (2013.01); *A61B 5/7207* (2013.01); *A61B 5/7435* (2013.01); *A61B 5/1116* (2013.01); *A61B 5/1121* (2013.01); *A61B 5/1122* (2013.01); *A61B 5/1124* (2013.01); *A61B 5/743* (2013.01); *A61B 2505/09* (2013.01); *A61B 2562/0219* (2013.01); *A61B 2562/0223* (2013.01)

(58) Field of Classification Search
CPC ... A61B 5/1127; A61B 5/1116; A61B 5/6823; A61B 5/743; A61B 5/7435; A61B 2505/09; A61B 2562/0219; A61B 2562/0223
See application file for complete search history.

(56) References Cited

U.S. PATENT DOCUMENTS

| | | | |
|---|---|---|---|
| 2011/0140897 A1* | 6/2011 | Purks | A61B 5/1038 340/573.1 |
| 2011/0313705 A1* | 12/2011 | Esser | A61B 5/112 702/104 |
| 2012/0000300 A1* | 1/2012 | Sunagawa | A61B 5/1116 73/865.4 |
| 2012/0101771 A1 | 4/2012 | Mori | |
| 2013/0123669 A1 | 5/2013 | Kinoshita et al. | |
| 2014/0024973 A1* | 1/2014 | Pettit | A61B 5/7275 600/595 |
| 2014/0032124 A1 | 1/2014 | Umer et al. | |

FOREIGN PATENT DOCUMENTS

| | | |
|---|---|---|
| JP | 2009-106391 A | 5/2009 |
| JP | 2010-193977 A | 9/2010 |
| JP | 2012-343 A | 1/2012 |
| JP | 2012-24449 A | 2/2012 |
| JP | 2013-59489 A | 4/2013 |
| JP | 2014-504932 A | 2/2014 |

OTHER PUBLICATIONS

International Search Report issued in PCT/JP2015/055928, dated May 19, 2015.

Extended European Search Report, dated Sep. 27, 2017, for European Application No. 15755345.4.

Lee et al., "3D spinal motion analysis during staircase walking using an ambulatory inertial and magnetic sensing system," Medical & Biological Engineering & Computing, vol. 49, No. 7, 2011 (published online Jan. 27, 2011), pp. 755-764, XP019919631.

Smeathers, "Measurement of transmissibility for the human spine during walking and running," Clinical Biomechanics, vol. 4, No. 1, 1989 (Feb. 1989), pp. 34-40, XP026177986.

* cited by examiner

METHOD FOR DETECTING AMBULATORY STATUS AND DEVICE FOR DETECTING AMBULATORY STATUS

FIELD OF TECHNOLOGY

The present invention relates to a method and a device for detecting an ambulatory status of a subject.

BACKGROUND TECHNOLOGY

In case of analyzing an ambulatory status, moving images, which have been photographed by a high speed camera, etc., are usually analyzed.

However, there are some problems, e.g., the high speed camera being expensive, a measuring range being limited within several meters square, a method for analyzing moving images being complex.

On the other hand, another conventional method for analyzing an ambulatory status by using motion sensors, e.g., acceleration sensors, without photographing moving images, has been developed.

For example, in a method for analyzing an ambulatory status disclosed in Patent Document 1, a plurality of sensors are provided to a hip joint between both feet and provided to knee joints and foot joints in a state where the joints are pinched between the sensors, so that walking data, e.g., joint angles, of a subject can be obtained on the basis of data from the sensors.

Further, in a walking evaluation device disclosed in Patent Document 2, acceleration sensors are attached to ankle parts of a subject, and frequency spectra of acceleration signals are analyzed on the basis of the acceleration data of the ankle parts measured by the acceleration sensors, so that ambulatory statuses, e.g., shuffling, sliding, can be evaluated.

PRIOR ART DOCUMENT

Patent Document

Patent Document 1: Japanese Laid-open Patent Publication No. 2012-343
Patent Document 2: Japanese Laid-open Patent Publication No. 2013-59489

DISCLOSURE OF THE INVENTION

Problems to be Solved by the Invention

In the above described conventional analyzing method and device, number of steps and walking cycles (walking pitches) can be easily measured. However, conditions of movement of a trunk of the subject while walking cannot be precisely analyzed.

Note that, in a rehabilitation facility, a physical therapist visually observes an ambulatory status of a subject and instructs the subject on the basis of the ambulatory status. When instructing the subject, the physical therapist attentions not only a lower body trunk, e.g., lower lumber vertebrae, near sacral bone, but also magnitude and balance of the movement.

However, the physical therapist needs a lot of experiences to analyze the ambulatory status on the basis of not only movements of limbs but also movements of the upper and lower body trunks, so it is difficult to perform such analysis.

Therefore, there is a problem of providing a method and a device for easily analyzing an ambulatory status including a movement of an upper body.

Thus, the present invention is invented to solve the above described problems, and an object of the present invention is to provide a method and a device for easily detecting an ambulatory status including a movement of an upper body, without complex operation of equipment, in a medical facility, e.g., rehabilitation facility.

Means for Solving the Problems

To achieve the above described object, the present invention has the following structures.

Namely, the method for detecting an ambulatory status of the present invention comprises a step of detecting the ambulatory status of a subject, by measuring conditions of movement in at least two places of the subject, including a lumber area and a thoracodorsal area, during detection of the ambulatory status of the subject.

With this method, conditions of an upper body of the subject can be known from conditions of movement of lumber area and thoracodorsal area, so that a proper judgement can be performed without gaining many actual experiences in, for example, a rehabilitation facility.

In the method, the lumber area may be near a flat surface of sacral bone from lower lumber vertebrae, and the thoracodorsal area may be near thoracodorsal area.

By detecting conditions of movement in at least the two places, i.e., near the flat surface of the sacral bone from the lower lumber vertebrae and near the apex of posterior curve of the thoracic vertebrae, the ambulatory status of the subject can be judged.

In the method, the conditions of movement in at least two places may be any of accelerations, speeds, positions, angular speeds and angles, or combinations thereof.

In the method, the conditions of movement in at least two places may be measured by analyzing images photographed by a high speed camera.

With this method, sensors, etc. need not be attached to the subject, so physical burden of the subject can be reduced.

In the method, the conditions of movement in at least two places may be measured on the basis of data measured by motion sensors provided to said two places.

In the method, each of the motion sensors may be any selected from an acceleration sensor, an angular speed sensor and a magnetic sensor, or a combination thereof.

The device for detecting ambulatory status of the present invention comprises: a monitor; motion sensors being respectively provided to two places of a subject, i.e., a lumber area and a thoracodorsal area; means for calculating conditions of movement in said two places on the basis of data measured by the motion sensors; and means for superposing the conditions of movement in said two places, which have been calculated by the calculating means, and displaying the superposed conditions on the monitor.

With this structure, the conditions of movement of the lumber area and the thoracodorsal area can be visually observed, so that a proper judgement can be performed without gaining many actual experiences in, for example, a rehabilitation facility.

In the device, each of the motion sensors may be any selected from an acceleration sensor, an angular speed sensor and a magnetic sensor, or a combination thereof.

In case that the motions sensors are acceleration sensors, the calculating means may extract only vibration components by filtering the data detected by the acceleration sensors, and the extracted vibration components may be integrated so as to calculate any of rocking accelerations, rocking speeds and rocking amounts.

By extracting only the vibration components from the data detected by the acceleration sensors, walking displacement in a walking direction can be removed, so that the correct ambulatory status can be known.

In case that the motions sensors are angular speed sensors, the calculating means may extract only vibration components by filtering the data detected by the angular speed sensors, and the extracted vibration components may be integrated so as to calculate any of rocking accelerations, rocking speeds and rocking amounts.

By extracting only the vibration components from the data detected by the angular speed sensors, walking displacement in a walking direction can be removed, so that the correct ambulatory status can be known.

In case that the motions sensors are angular speed sensors, the calculating means may calculate angular speeds from the data detected by the angular speed sensors, or may calculate angles by integrating the data detected by the angular sensors.

In case that the motions sensors are magnetic sensors, the calculating means may calculate angles from the data detected by the magnetic sensors.

Further, in the device, the displaying means may make Lissajous figures of said two places, in a horizontal plane, on the basis of any of rocking accelerations, rocking speeds and rocking amounts calculated by the calculating means, may superpose the Lissajous figures of said two places and may display the superposed figures on the monitor.

With this structure, the ambulatory status of the subject, especially the lumber area and the thoracodorsal area, can be visually confirmed as a highly clear image.

In the device, the displaying means may make Lissajous figures of said two places, in a horizontal plane, on the basis of rocking accelerations or rocking speeds calculated by the calculating means, may superpose the Lissajous figures of said two places and may display the superposed figures on the monitor.

With this structure, the ambulatory status of the subject, especially the lumber area and the thoracodorsal area, can be visually confirmed as a highly clear image.

In the device, each of the motion sensors may be constituted by a three-axis acceleration sensor and a three-axis angular speed sensor, the calculating means may detect the gravity direction on the basis of the data detected by the three-axis acceleration sensor and may calculate angular speeds or angles in the three-dimensional orthogonal coordinate system, i.e., in the gravity direction, a walking direction in a horizontal plane and a left/right direction in the horizontal plane, on the basis of the detected gravity direction, from the data detected by the three-axis acceleration sensors, and the displaying means may make Lissajous figures on the basis of the angular speeds or angles in the gravity direction, the walking direction in the horizontal plane and the left/right direction in the horizontal plane, may superpose the Lissajous figures of the motion sensors of said two places in the walking direction in the horizontal plane and the left/right direction in the horizontal plane respectively, and may display the superposed figures on the monitor.

With this structure, the ambulatory status can be further correctly confirmed.

In the device, the calculating means may calculate conditions of movement in said two places from a reference posture of the subject being stationary to an ordinary posture of the subject being stationary, and the displaying means may correct the conditions of movement in said two places from the reference posture of the subject to the ordinary posture of the subject being stationary, which have been calculated by the calculating means, and may display the corrected conditions on the monitor when superposing the conditions of movement in said two places, which have been measured by the motion sensors on the basis of the measured data, and displaying the superposed conditions on the monitor.

With this structure, a positional relationship between the motion sensors (e.g., position shift, inclination, twisting) can be calculated, so that physical features of the subject other than walking, e.g., shoulder lowering, round shoulders, can be judged. When displaying the conditions of movement while walking, proper judgement for rehabilitation can be performed by further displaying the above described physical features on the monitor.

Note that, the reference posture means a posture in a state where the two motion sensors are provided on a vertical axial line of the subject, which is located at near the left right center of the subject, and axial directions of the two motion sensors are coincided.

In the device, the calculating means may calculate positions of the motion sensors with respect to a center axis of the subject along the vertical direction while walking, and the displaying means may correct the positions of the motion sensors, which have been calculated by the calculating means, and may display the corrected positions on the monitor when superposing the conditions of movement in said two places, which have been measured by the motion sensors on the basis of the measured data, and displaying the superposed conditions on the monitor.

With this structure, the positional relationship between the motion sensors while walking (e.g., position shift, inclination, twisting) can be calculated, so that the physical features of the subject other than walking, e.g., shoulder lowering, round shoulders, can be judged. When displaying the conditions of movement while walking, proper judgement for rehabilitation can be performed by further displaying the above described physical features on the monitor.

In the device, the displaying means may display a connection line, which connects same time points in the Lissajous figures of the motion sensors of said two places to each other, and may move the connection line with the lapse of time.

With this structure, linked movement of the lumber area and the thoracodorsal area can be displayed and easily understood.

In the device, the displaying means may display images of soles of both feet of the subject on the monitor and specified places of the soles of the both feet, the calculating means may calculate impact values applied to the specified places, and the displaying means may display the calculated impact values on the monitor.

With this structure, the impact values applied to the both feet can be known, so that the ambulatory status can be further correctly confirmed.

Another device for detecting ambulatory status of the present invention comprises: a monitor; markers being provided to at least two places of a subject including a lumber area and a thoracodorsal area; a plurality of high speed cameras for photographing the markers; and means for superposing conditions of movement of the markers, which have been photographed by the high speed cameras, and displaying the superposed conditions on the monitor.

With this structure, the conditions of movement of the lumber area and the thoracodorsal area can be visually observed, so that a proper judgement can be performed without gaining many actual experiences in, for example, a rehabilitation facility.

The device may further comprise: motion sensors being respectively provided to said two places of the subject, i.e., a lumber area and a thoracodorsal area; and means for calculating conditions of movement in said two places on the basis of data measured by the motion sensors, and the displaying means may superpose the conditions of movement of the markers, which have been photographed by the high speed cameras, and may display the superposed conditions on the monitor, the displaying means may further superpose conditions of movement in said two places, which have been photographed by calculating means, and may display the calculated conditions on the monitor.

With this structure, the conditions of movement of the lumber area and the thoracodorsal area can be easily visually confirmed on the basis of not only the conditions of movement of the markers photographed by the high speed cameras but also the conditions of movement measured by the motion sensors.

In the device, the calculating means may calculate a positional relationship between the motion sensors, which have been photographed, by the high speed cameras, while the subject being stationary, and the displaying means may correct the conditions of movement in said two places on the basis of the positional relationship between the motion sensors, which has been calculated by the calculating means, and may display the corrected conditions on the monitor when superposing the conditions of movement of said two places, which have been detected by the motion sensors on the basis of the measured data, and displaying the superposed conditions on the monitor.

With this structure, the positional relationship between the motion sensors in a still state (e.g., position shift, inclination, twisting) can be calculated, so that the physical features of the subject other than walking, e.g., shoulder lowering, round shoulders, can be judged. When displaying the conditions of movement while walking, proper judgement for rehabilitation can be performed by further displaying the above described physical features on the monitor.

Effects of the Invention

In the method and the device for detecting ambulatory state of the present invention, a proper judgement can be performed without gaining many actual experiences in, for example, a rehabilitation facility.

EMBODIMENTS OF THE INVENTION

First Embodiment

An embodiment of the present invention will now be described in detail with reference to the accompanying drawings.

Figure 1:
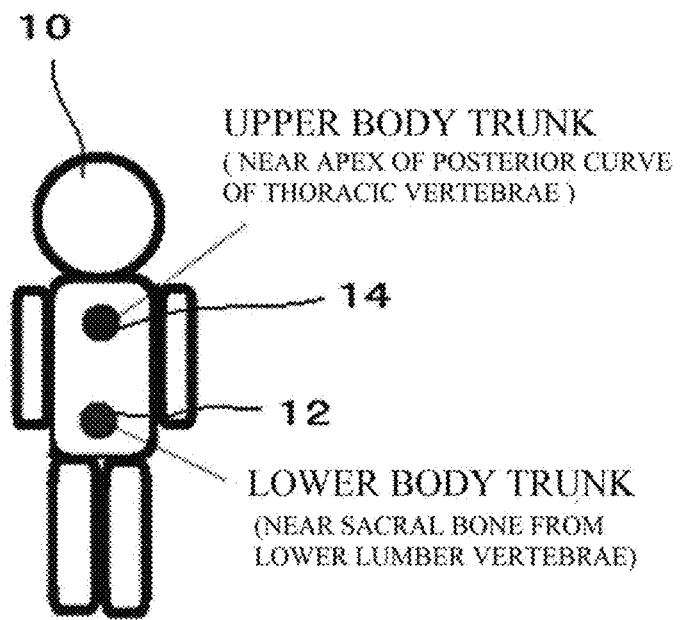
FIG. 1 is an explanation view of a subject whose ambulatory status is detected by the method for detecting an ambulatory status.
Figure 2:
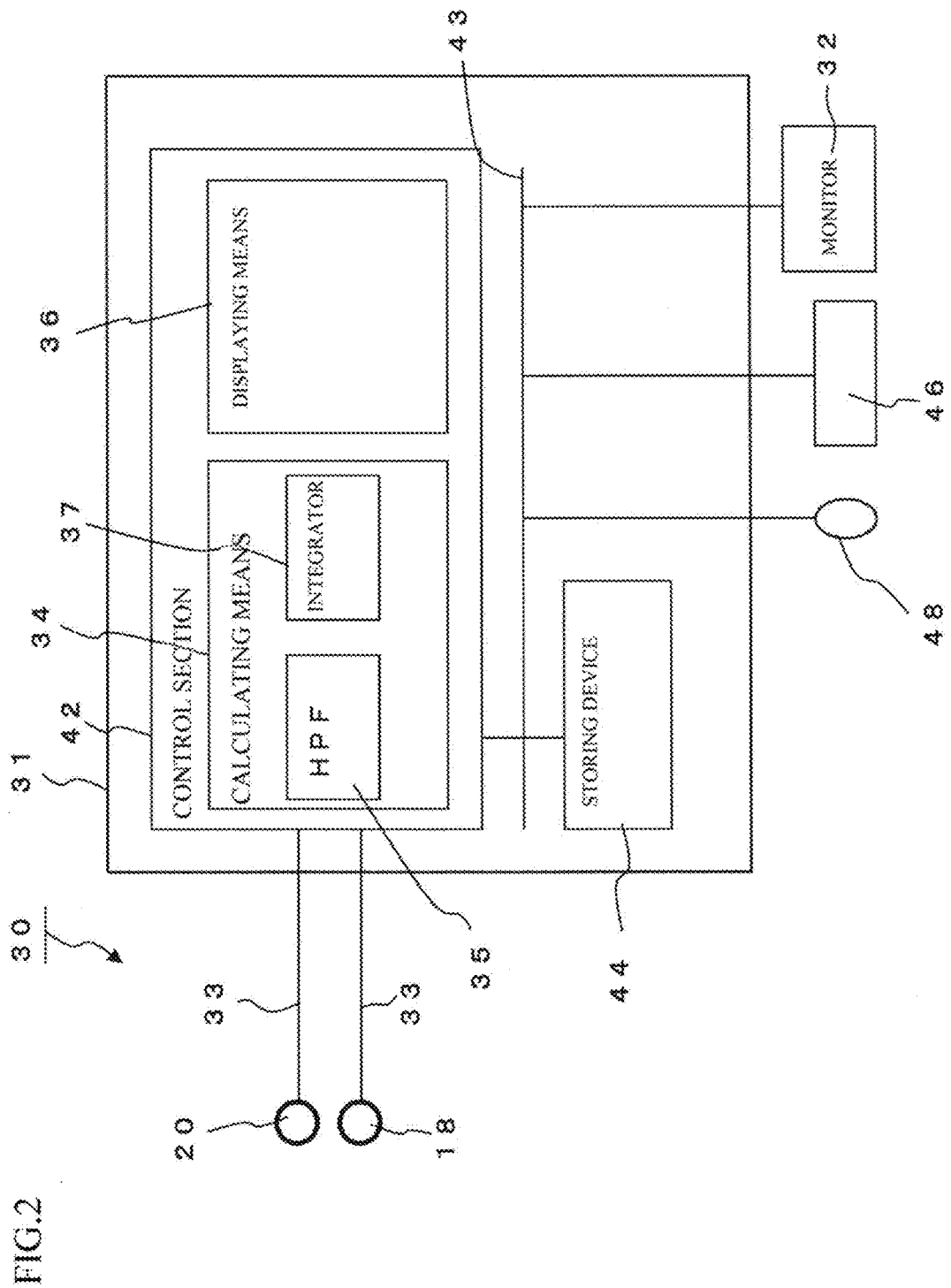
FIG. 2 is an explanation view of a first embodiment of the device for detecting an ambulatory status.

FIG. 1 is an explanation view of a subject 10 whose ambulatory status will be detected. FIG. 2 is a schematic explanation view of the device for detecting the ambulatory status.

In the present embodiment, conditions of movement of the subject are measured in two places, i.e., a lumber area 12 and a thoracodorsal area 14. A concrete example of the lumber area 12 is near a sacral bone from lower lumber vertebrae. The sacral bone locates in a lower part of vertebra and constitutes pelvis. The thoracodorsal area 14 is near an apex of a posterior curve of thoracic vertebrae. The thoracic vertebra is a part of the vertebra and locates near scapulars. Note that, the conditions of movement must be measured at said two places, but the conditions of movement may be further measured in three places or more, e.g., head part.

In case of detecting an ambulatory status, movement of, especially, an upper body trunk can be easily known by measuring conditions of movement of the lumber area and the thoracodorsal area, not legs, so that the ambulatory status can be correctly known.

In the present embodiment, the device 30 for detecting an ambulatory status has: motions sensors 18 and 20, which are respectively provided to the lumber area 12 and the thoracodorsal area 14 of the subject; a main device section 31; and a monitor 32.

In the present embodiment, three-axis acceleration sensors 18 and 20 are provided to the lumber area 12 and the thoracodorsal area 14, as examples of the motion sensors, so as to measure the conditions of movement in the lumber area 12 and the thoracodorsal area 14.

Accelerations of three axes, i.e., an x-axis which is a left/right direction in a horizontal plane, a y-direction which is a walking direction in the horizontal plane and a z-direction which is the vertical direction, can be measured in said places.

The two three-axis acceleration sensors 18 and 20 are connected to the main device section 31 of the device 30 for detecting an ambulatory status and capable of data-communicating therewith. The three-axis acceleration sensors 18 and 20 are connected to the main device section 31 by, for example, data communication cables 33, so that data communication can be performed.

Next, a concrete example of the main device section 31 of the device 30 for detecting an ambulatory status will be explained.

The main device section 31 may be an ordinary computer.

The computer 31 has a control section 42 which runs on the basis of control programs. The control section 42 is constituted by a CPU, ROMs, RAMs, etc., not shown. The control section 42 is connected to a storing unit 44, e.g., hard disk drive unit, via an inner bus 43. Note that, the storing device 44 is not limited to the hard disk drive unit.

Note that, a key board and a pointing device, e.g., a mouse 48, which act as input units, are connected to the control section 42 via the inner bus 43.

The control section 42 calculates conditions of movement in said two places, on the basis of data sent from the three-axis acceleration sensors 18 and 20, so as to realize calculating means 34.

Further, the control section 42 superposes the conditions of movement, which have been calculated by the calculating means 34, and displays the superposed conditions on the monitor 32, so as to realize displaying means 36.

Acceleration data of the two three-axis acceleration sensors 18 and 20 are inputted to the calculating means 34.

The calculating means 34 includes a high-pass filter 35, which filters the acceleration data measured in said two places. Low frequency components of the acceleration data are removed by the high-pass filter 35, so that only high frequency components thereof are obtained.

A reason of performing the filtering process will be explained. In case of using the acceleration data, walking displacements are included, so the ambulatory status should be judged on the basis of the data excluding the walking displacements. Therefore, in the calculating means 34, the high-pass filter 35 removes the walking displacements, which correspond to the low frequency components, so that only vibration components, which are high frequency components, can be extracted.

Note that, in the calculating means 34, the filtering means for removing the walking displacements, i.e., low frequency components, is not limited to the high-pass filter, and other filtering means together using angular speeds and signals from magnetic sensors may be employed.

Further, the calculating means 34 has an integrator 37 for integrating vibration components extracted in the filtering process.

Note that, in the specification and claims of the present invention, the vibration components of the acceleration data (not integrated) indicate a rocking acceleration; the vibration components of the acceleration data integrated once indicate a rocking speed; and the vibration components of the acceleration data integrated twice indicate a rocking amount.

The displaying means 36 of the present embodiment makes Lissajous figures of said two places, in a horizontal plane, on the basis of the rocking accelerations, the rocking speeds or the rocking amounts calculated by the calculating means 34, superposes the Lissajous figures of said two places and displays the superposed figures on the monitor 32.

The Lissajous figure is a curved line drawn by mutually combining single vibrations in the vertical direction.

In the present embodiment, the vibration components are extracted by the calculating means 34 as described above, so the Lissajous figures can be made.

Figure 3:
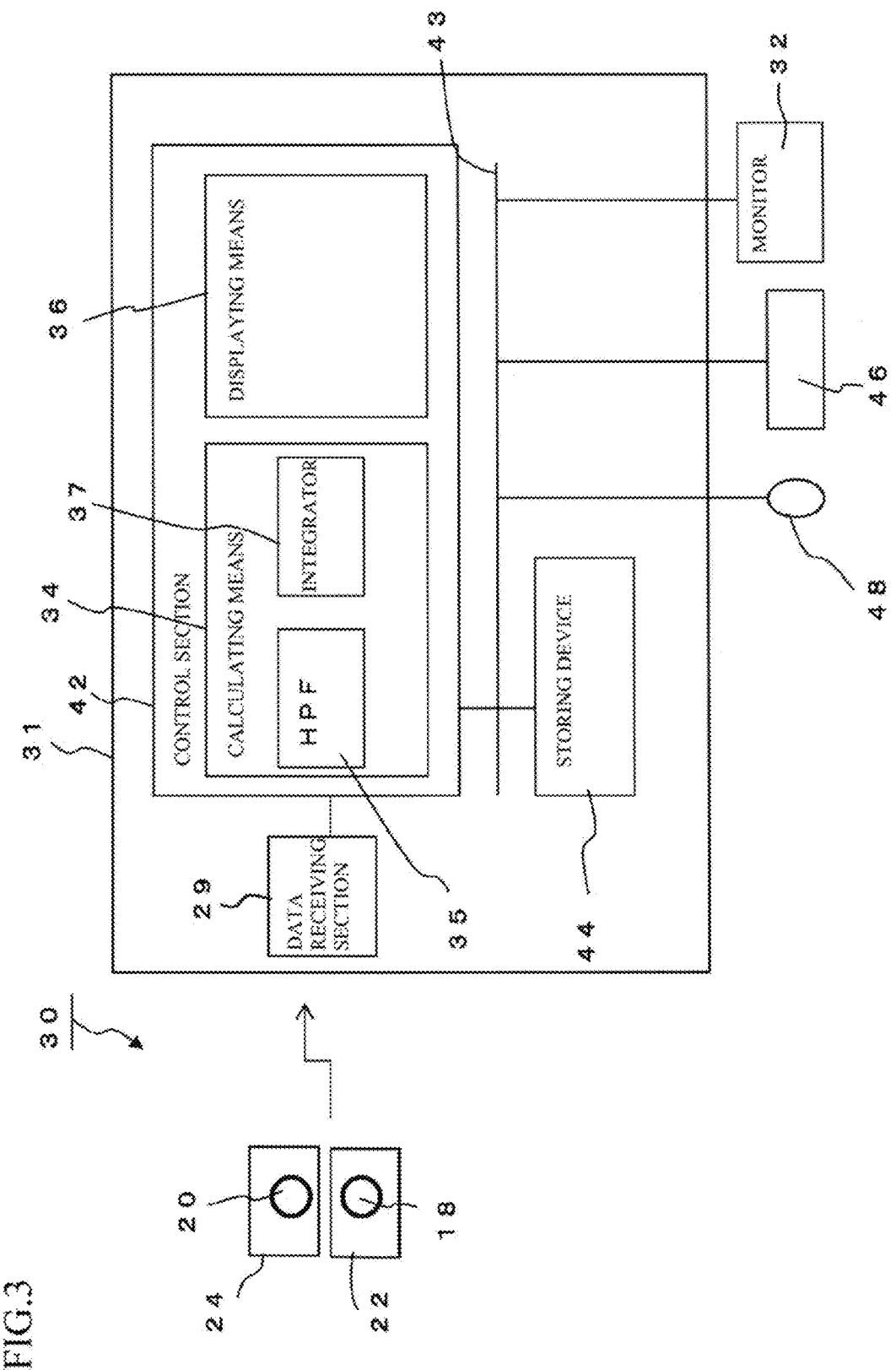
FIG. 3 is an explanation view of the device for detecting an ambulatory status which has a radio communication function.
Figure 4:
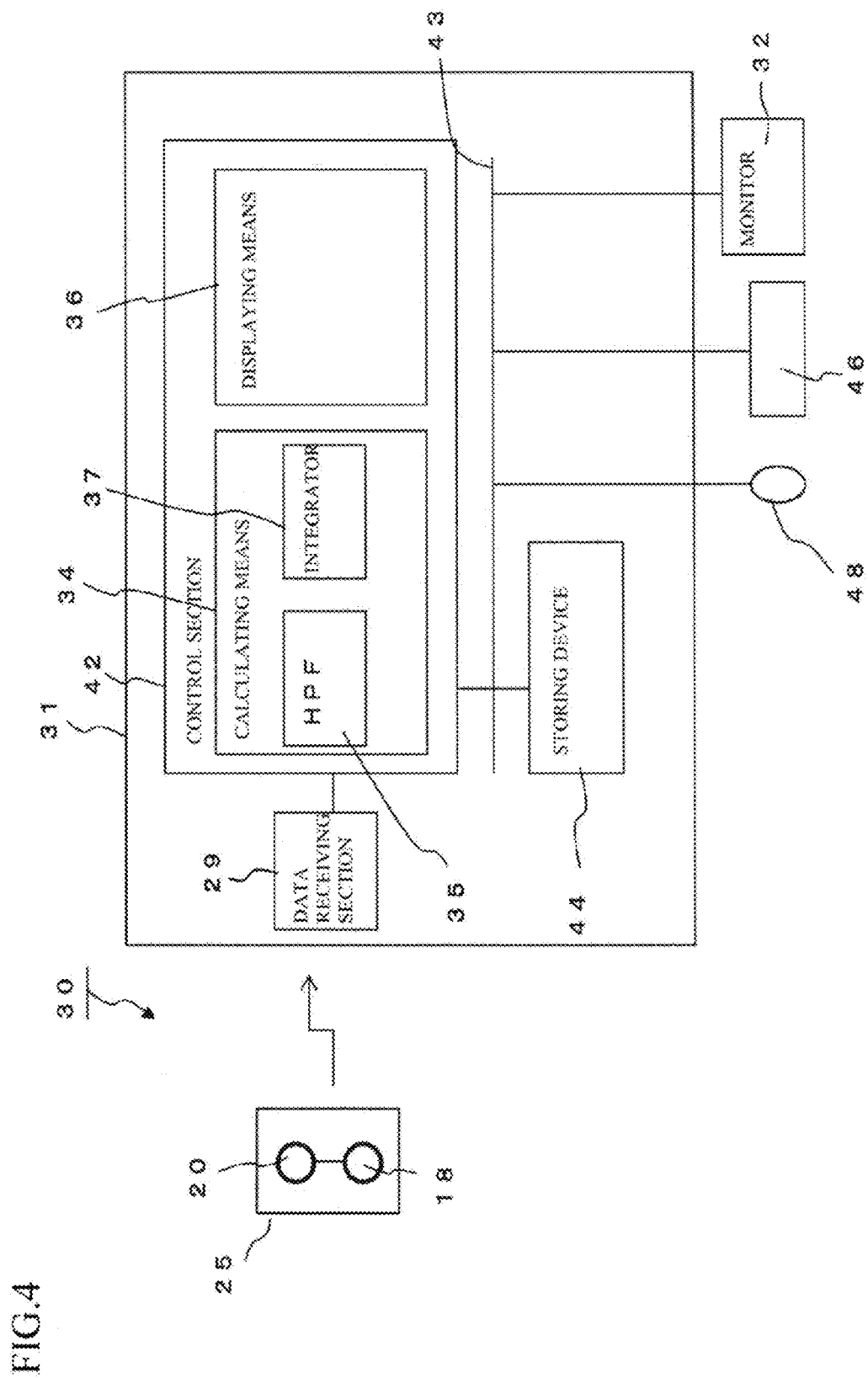
FIG. 4 is an explanation view of another example of the device for detecting an ambulatory status which has a radio communication function.

Other embodiments of the detecting device of the preset invention are schematically shown in FIGS. 3 and 4. Note that, the structural elements shown in FIG. 2 are assigned the same symbols and explanation will be omitted.

In FIG. 3, the three-axis acceleration sensors 18 and 20 are data-communicated with the main device section 31 by radio communication means, not by communication cables, etc.

The three-axis acceleration sensors 18 and 20 respectively have data transmitting sections 22 and 24, so that the detected acceleration data can be radio-transmitted. Further, the main device section 31 has a data receiving section 29, which receives the acceleration data radio-transmitted from the data transmitting sections 22 and 24.

For example, Bluetooth (registered trademark) may be employed as the radio communication means.

In FIG. 4 too, the three-axis acceleration sensors 18 and 20 can be radio-communicated with the main device section 31 so as to transmit and receive the data, but the three-axis acceleration sensors 18 and 20 are connected to one data transmitting section 25, so the data from the two three-axis acceleration sensors 18 and 20 can be transmitted from the one data transmitting section 25.

The main device section 31 has the data receiving section 29, which receives the acceleration data radio-transmitted from the data transmitting section 25.

Figure 5:
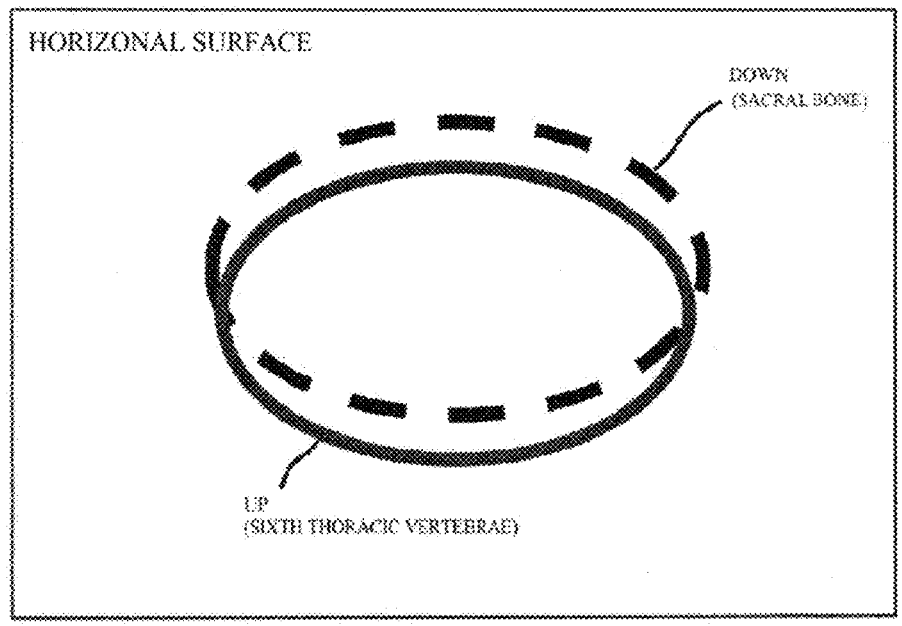
FIG. 5 is a schematic view of Lissajous figures displayed by the detecting device of the first embodiment.
Figure 6:
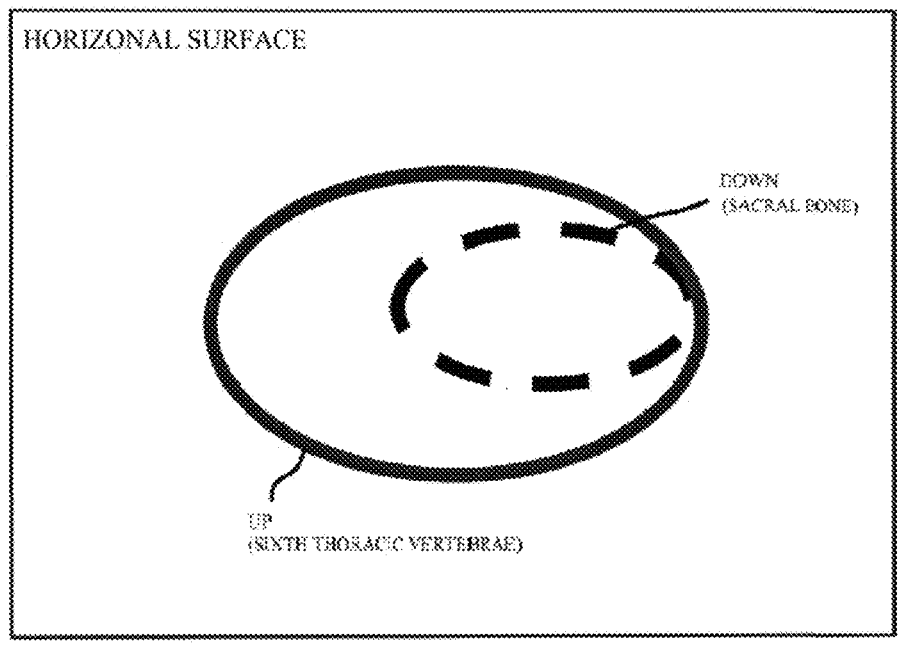
FIG. 6 is a schematic view of Lissajous figures displayed by the detecting device of the first embodiment.
Figure 7:
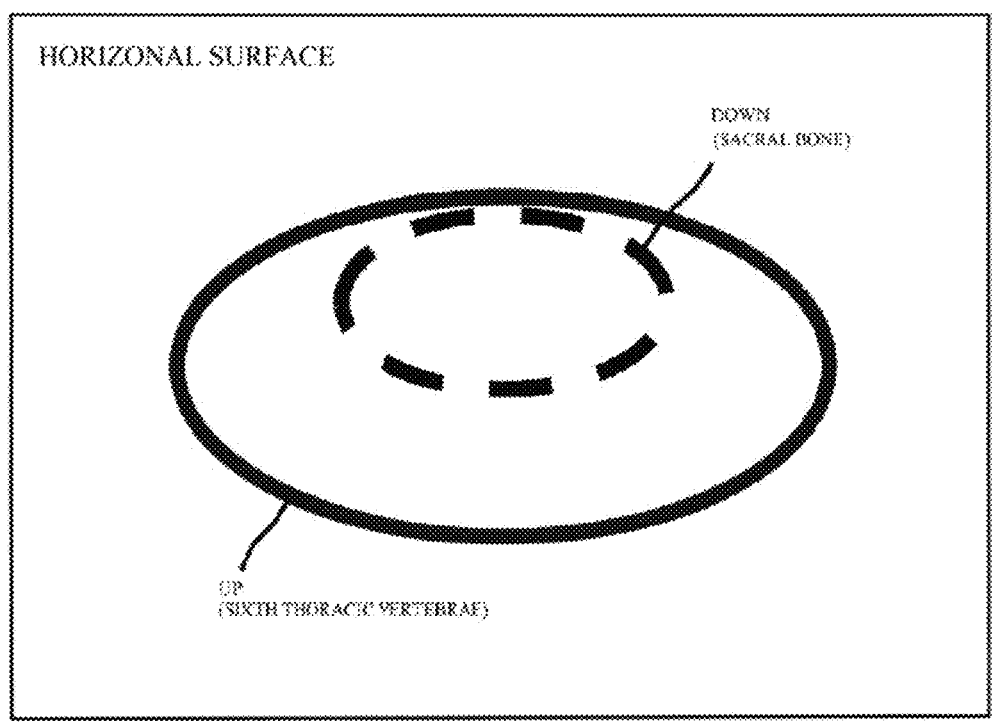
FIG. 7 is a schematic view of Lissajous figures displayed by the detecting device of the first embodiment.

The Lissajous figures made by the displaying means 36 are schematically shown in FIGS. 5-7.

In each of the Lissajous figures of the present embodiment, a horizontal axis indicates a left/right direction in a horizontal plane and a vertical axis indicates a walking direction, and the figures show rocking amounts of the lumber area 12 (near the sacral bone) and the thoracodorsal area 14 (near the sixth thoracic vertebrae).

In FIG. 5, the rocking amounts of the lumber area 12 (near the sacral bone) and the thoracodorsal area 14 (near the sixth thoracic vertebrae) are shown as ellipse circles of the same size. The two ellipse circles are almost not shifted to each other and located at a position near the same. The ellipse circle of the lumber area 12 (near the sacral bone) is located slightly forward and the ellipse circle of the thoracodorsal area 14 (near the sixth thoracic vertebrae) is located slightly backward with respect to the walking direction.

In case that the rocking amounts of the lumber area 12 (near the sacral bone) and the thoracodorsal area 14 (near the sixth thoracic vertebrae) are almost same and they are almost not shifted in the left/right direction, the ambulatory status is judged as a good status.

In FIG. 6, the rocking amount of the lumber area 12 (near the sacral bone) is shown as a slightly small ellipse circle. The rocking amount of the thoracodorsal area 14 (near the sixth thoracic vertebrae) is shown as a large ellipse circle, which includes the rocking amount of the lumber area 12 (near the sacral bone) inside. The rocking amount of the thoracodorsal area 14 (near the sixth thoracic vertebrae) largely expands leftward with respect to the rocking amount of the lumber area 12 (near the sacral bone).

In case that such Lissajous figures are made, a displacement of near the thoracic vertebrae is shifted leftward, so it is assumed that an upper body is largely inclined leftward when a left foot contacts the ground. Therefore, it is judged that there is a problem in a standing period of the left foot (a period while the left foot contacts the ground).

In FIG. 7, the rocking amount of the lumber area 12 (near the sacral bone) is shown as a slightly small ellipse circle. The rocking amount of the thoracodorsal area 14 (near the sixth thoracic vertebrae) is shown as a large ellipse circle, which includes the rocking amount of the lumber area 12 (near the sacral bone) inside, and largely expands in the left/right direction. Unlike the example shown in FIG. 6, the both rocking amounts are not shifted in the left/right direction.

In case that such Lissajous figures are made, it is known that a displacement of near the thoracic vertebrae is extremely large (especially in the left/right direction). Therefore, it is assumed that muscles of the lower body trunk are weakened and a driving force of walking is generated by largely swinging the upper body.

Note that, the Lissajous figures of FIG. 5-7 show the rocking amounts (the values obtained by integrating the vibration components obtained by filtering the acceleration data twice), and the above described rocking accelerations and rocking speeds can be shown as Lissajous figures.

Second Embodiment

Figure 8:
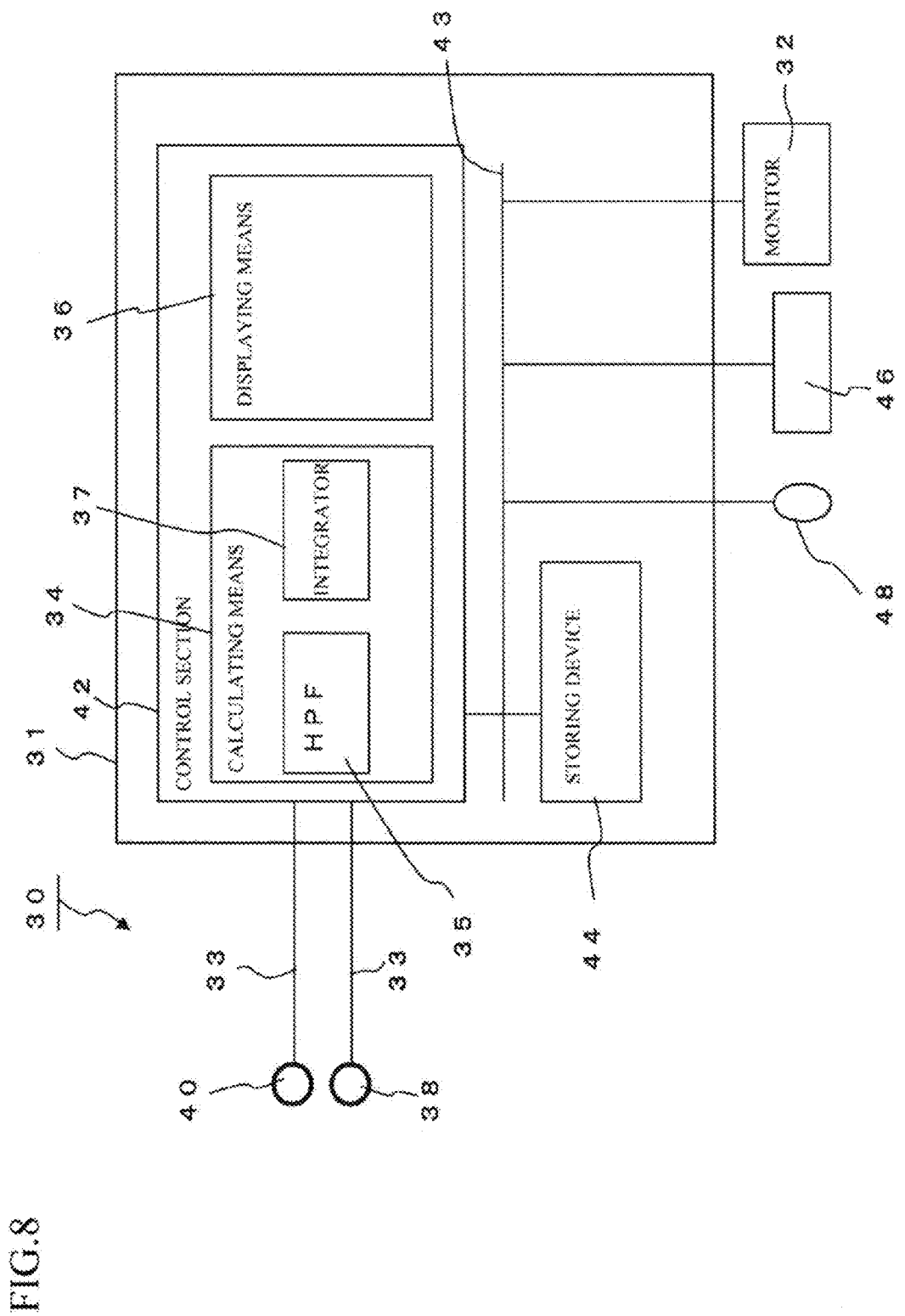
FIG. 8 is an explanation view of a second embodiment of the device for detecting an ambulatory status.

In the above described First Embodiment, the three-axis acceleration sensors are employed as the motion sensors. The present embodiment, in which three-axis angular speed sensors are employed as the motion sensors, will be explained with reference to FIG. 8.

Note that, the structural elements described in the former embodiment are assigned the same symbols and explanation will be omitted.

In case of employing the three-axis angular speed sensors as the motion sensors, the motion sensors are respectively provided to the lumber area 12 and the thoracodorsal area 14, and detected angular speed data are sent to the calculating means 34.

The angular speed data of the three-axis angular speed sensors 38 and 40 provided in said two places are inputted to the calculating means 34.

The calculating means 34 includes the high-pass filter 35, which filters the angular speed data measured in said two places. Low frequency components of the angular speed data are removed by the high-pass filter 35, so that only high frequency components thereof are obtained.

Further, the calculating means 34 has the integrator 37 for integrating vibration components extracted in the filtering process.

Note that, in the specification and claims of the present invention, the vibration components of the angular speed data (not integrated) indicate a rocking angular speed; and the vibration components of the angular speed data integrated once indicate a rocking angle.

Note that, the three-axis angular speed sensors 38 and 40 may be data-communicated with the main device section 31 by radio communication means, not by a communication cables, etc. In this case, the structure shown in FIG. 3 or 4 may be employed, so explanation will be omitted.

The displaying means 36 of the present embodiment makes Lissajous figures of said two places, in the horizontal plane, on the basis of the rocking angular speeds and the rocking angles calculated by the calculating means 34, superposes the Lissajous figures of said two places and displays the superposed figures on the monitor 32.

Note that, examples of the Lissajous figures are not shown, but they are similar to those of the First Embodiment which are shown in FIGS. 5-7.

In comparison with the acceleration data, the angular speed data are sometimes less influenced by walking displacements.

Therefore, the displaying means 36 may superpose the angular speed data of said two places and display the superposed data on the monitor 32 without filtering or integrating the angular speed data by the calculating means 34.

Note that, in this case, the calculating means 34 in the control section 42 may be omitted.

Figure 9:
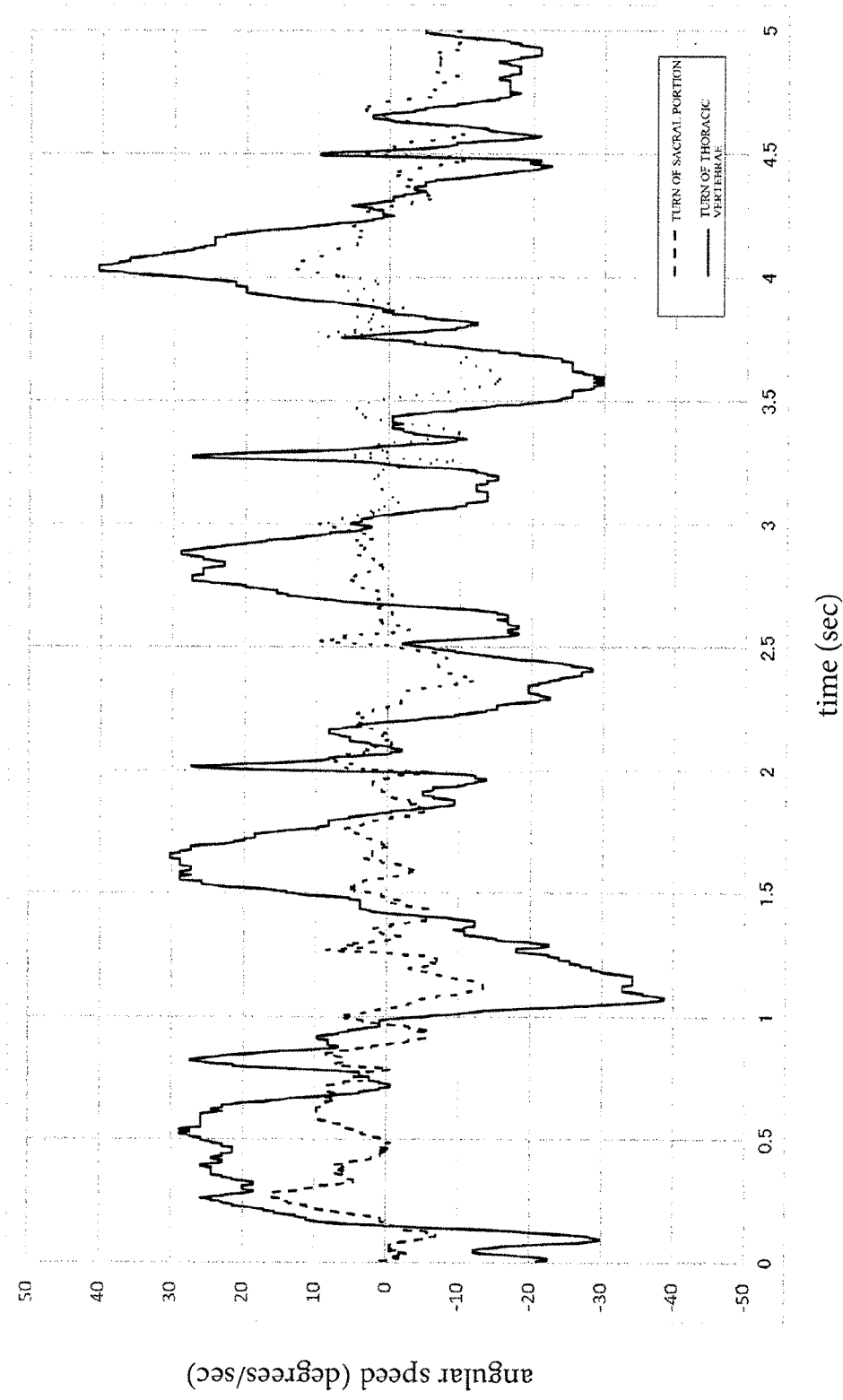
FIG. 9 is an example of a screen displayed on the basis of angular speed data.

An example of a display screen of the monitor, in which the angular speed data without being filtered and integrated are displayed, is shown in FIG. 9.

In FIG. 9, the horizontal axis of the graph indicates "time (sec.)" and the vertical axis thereof indicates "angular speed (degrees/sec.)".

There are four high peaks in the graph. The peak appears when taking one step, so the graph shows that the subject has walked four steps.

In this example, the angular speed near the sacral bone is slow, so it is judged that at least the lumber area is not twisted; but turn near the thoracic vertebrae is large, so it is judged that the subject walks with twisting the upper body trunk.

Further, the calculating means 34, to which the angular speed data have been inputted, may integrate the data once, without filtering the data, to obtain the angle data, and may display conditions of movement, on the basis of the angle data, on the monitor 32.

Figure 10:
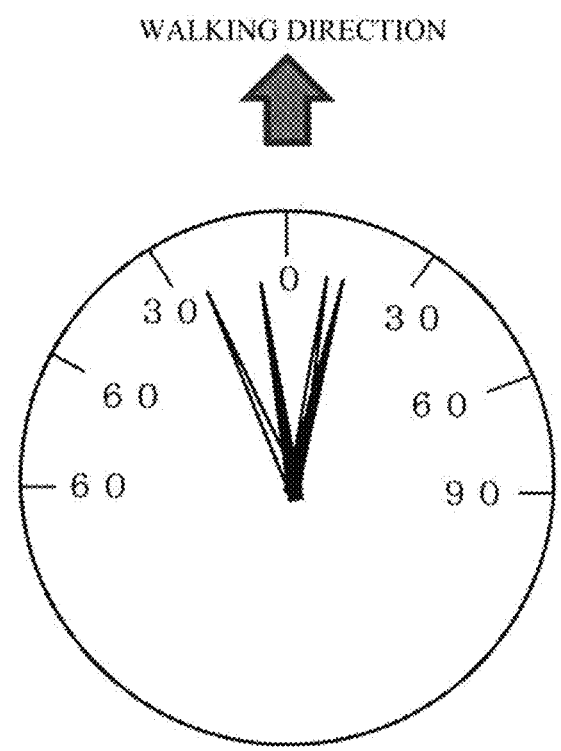
FIG. 10 is an example of a screen displayed on the basis of angle data.

An example of the screen of the monitor, in which the angle data obtained by integrating once, without being filtered, are displayed, is shown in FIG. 10.

In FIG. 10, four hands indicating right and left directions are extended from a center of a circle, an upper side of the drawing is a walking direction, and scales of 30 degrees, 60 degrees and 90 degrees, with respect to the center of the circle, are provided on the right and left sides.

Two hands of the four indicate angles of the lumber area, and the rest hands indicate angles of the thoracodorsal area. The two hands of the lumber area or the thoracodorsal area respectively indicate maximum angles in the right direction and the left direction.

With this method, twist of the upper body while walking can be judged.

Third Embodiment

Figure 11:
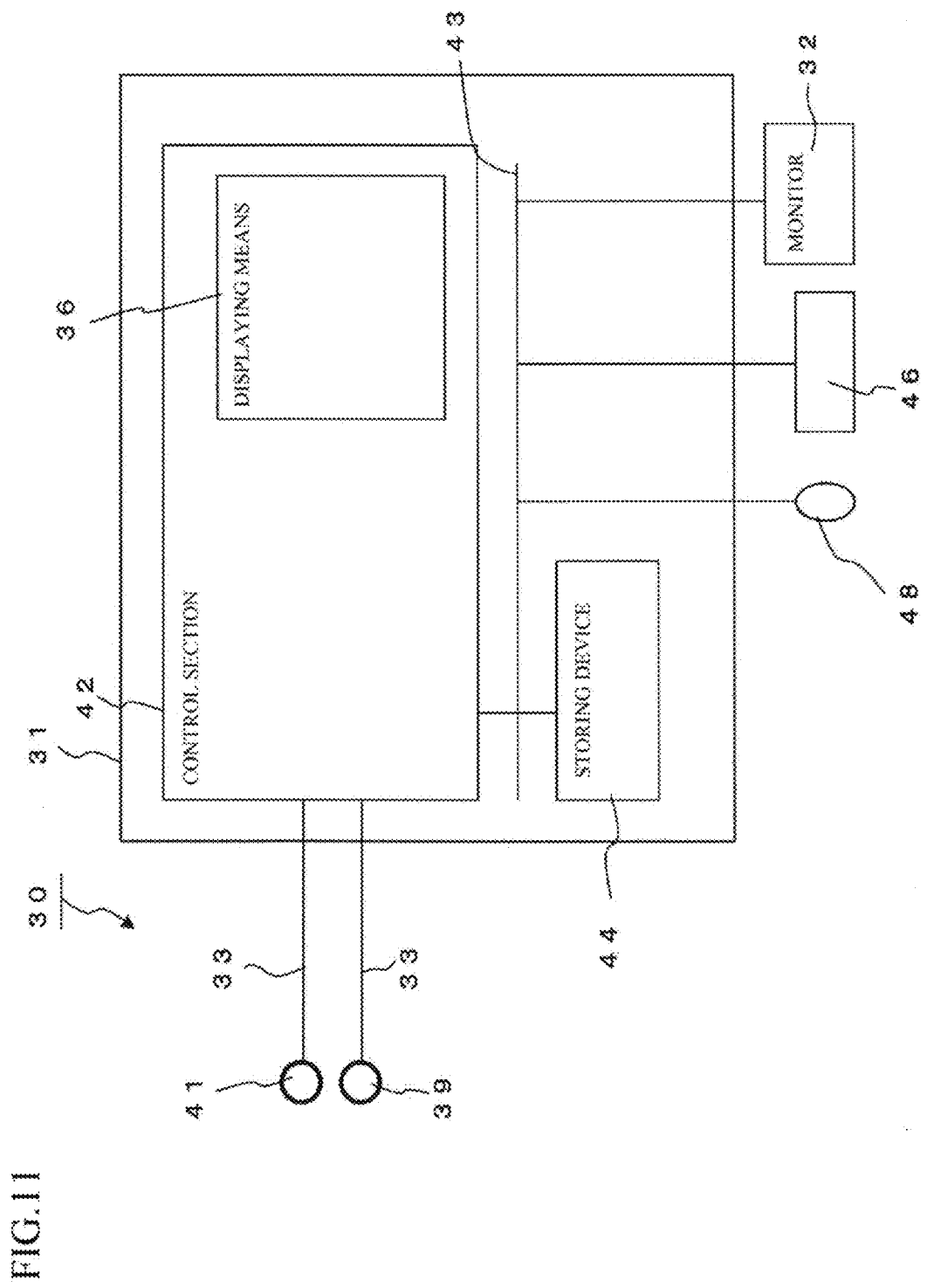
FIG. 11 is an explanation view of a third embodiment of the device for detecting an ambulatory status.

An embodiment, in which three-axis magnetic sensors are employed as the motion sensors, will be explained with reference to FIG. 11.

Note that, the structural elements described in the former embodiments are assigned the same symbols and explanation will be omitted.

Magnetic sensors can detect angle components of moving parts by using the fact that magnetic field of earth magnetism is greater. Therefore, in the present embodiment too, the three-axis magnetic sensors detect angle data.

In case that the three-axis magnetic sensors 39 and 41 are employed as the motion sensors too, the sensors are respectively provided in the lumber area 12 and the thoracodorsal area 14, and the detected angle data are sent to the control section 42.

In the present embodiment, the angler data may be used without being processed, and the displaying means 36 may superpose the angle data of said two places and may display them on the monitor 32.

In this case, the calculating means 34 for filtering and integrating the data may be omitted.

Note that, the three-axis magnetic sensors 39 and 41 may be data-communicated with the main device section 31 by radio communication means, not by communication cables, etc. In this case, the structure shown in FIG. 3 or 4 may be employed, so explanation will be omitted.

The screen of the monitor indicating the angle data may be similar to the example shown in FIG. 10, so explanation will be omitted.

Fourth Embodiment

An embodiment, in which three-axis acceleration sensors and three-axis angular speed sensors are employed as the motion sensors, will be explained.

Namely, a motion sensor 56 is constituted by the three-axis acceleration sensor and the three-axis angular speed sensor, and provided to near the sacral bone; and a motion sensor 58 is also constituted by the three-axis acceleration sensor and the three-axis angular speed sensor, and provided to near the thoracic vertebrae.

Figure 12:
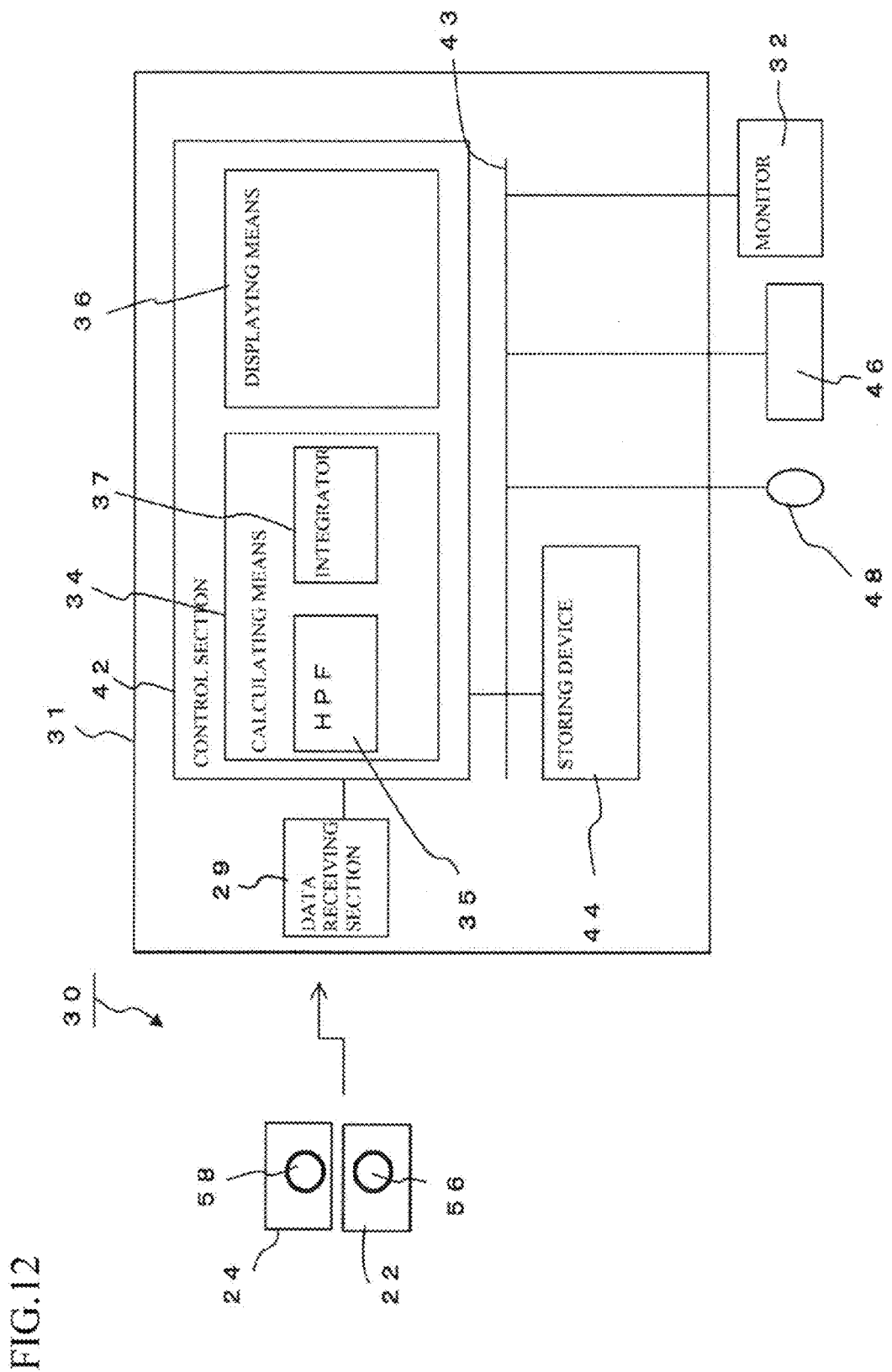
FIG. 12 is an explanation view of a fourth embodiment of the device for detecting an ambulatory status.

The device for detecting an ambulatory status of the present embodiment is shown in FIG. 12.

Note that, the structural elements described in the former embodiments are assigned the same symbols and explanation will be omitted.

The motion sensors 56 and 58 respectively have the data transmitting sections 22 and 24, so that the detected acceleration data can be radio-transmitted. Further, the main device section 31 has the data receiving section 29, which receives the acceleration data transmitted from the data transmitting sections 22 and 24. For example, Bluetooth (registered trademark) may be employed as the radio communication means.

The main device section 31 may be an ordinary computer. The computer 31 has the control section 42 which runs on the basis of the control programs.

Figure 13:
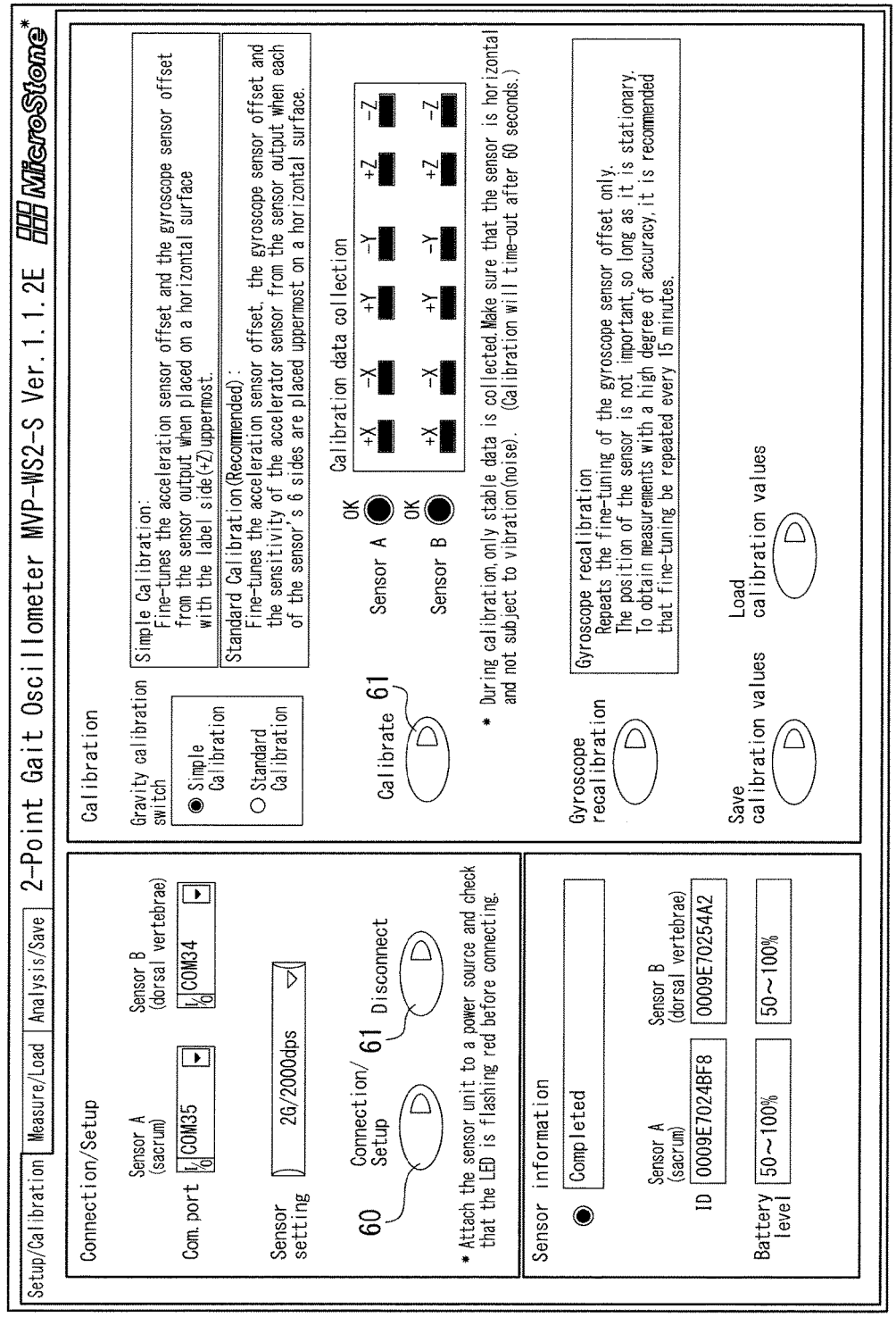
FIG. 13 is an explanation view of a setting screen for setting each of motion sensors, which is displayed by the detecting device of the fourth embodiment.

By starting the control program previously stored in the control section 42, an operation screen shown in FIG. 13 is displayed on the monitor 32. The operation screen is used to set and correct the motion sensors 56 and 58.

By pushing a connecting/setting button 60 shown in an upper-left part of the screen shown in FIG. 13 with, for example, the mouse 48, the control section 42 connects and sets the motion sensors 56 and 58.

A sensor turn-off button 61 is provided to near the connecting/setting button 60.

Instructions for correction are shown in a right part of the screen shown in FIG. 13.

A purpose of the instructions is to securely detect the gravity direction and the horizontal direction perpendicular to the gravity direction, and an operator can select a simple correction manner or a standard correction manner.

In each of the simple correction manner and the standard correction manner, the motion sensors 56 and 58 are mounted on a horizontal plane so as to detect the gravity direction. By pushing a correction button 62 with the mouse 48, etc., the control section 42 executes the correction. Corrected data collection lamps, which respectively correspond to the motion collection sensors 56 and 58, are provided to near the correction button 62.

Next, the actual detecting actions will be explained.

The motion sensor 56 is provided to near the sacral bone of the subject, the motion sensor 58 is provided to near the sixth thoracic vertebrae thereof, and the control section 42 automatically collects walking data of a prescribed time period when the subject walks.

Note that, when the motion sensors 56 and 58 are attached to the subject, the motion sensors 56 and 58 must be directed in the assigned directions. For example, in the motion sensors 56 and 58, the attaching directions are indicated as follows: X-direction being a right direction; Y-direction being an upper direction; and Z-direction being a walking direction.

Acceleration data in the X-direction, acceleration data in the Y-direction and acceleration data in the Z-direction, angular speed data in the X-direction, angular speed data in the Y-direction and angular speed data in the Z-direction are transmitted from the motion sensor 56 provided to near the sacral bone, at regular time intervals (e.g., 5 milliseconds), to the data receiving section 29.

Similarly, acceleration data in the X-direction, acceleration data in the Y-direction and acceleration data in the Z-direction, angular speed data in the X-direction, angular speed data in the Y-direction and angular speed data in the Z-direction are transmitted from the motion sensor 58 provided to near the sixth thoracic vertebrae, at regular time intervals (e.g., 5 milliseconds), to the data receiving section 29.

The data received by the data receiving section 29 are displayed, without being processed, by the displaying means 36.

Figure 14:
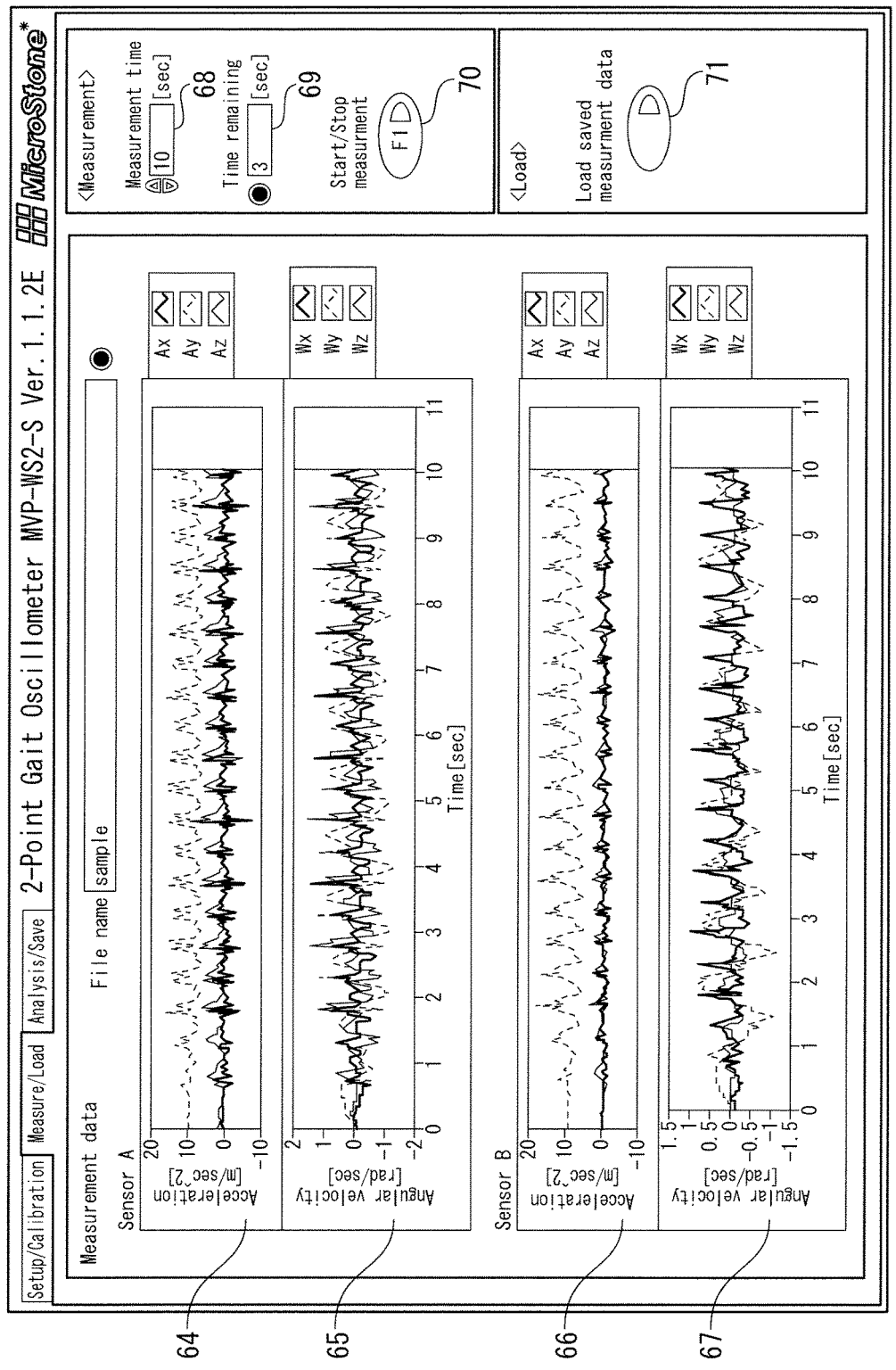
FIG. 14 is an explanation view of a screen showing data measured by the motion sensors of the detecting device of the fourth embodiment.

An example of displaying the detected data is shown in FIG. 14.

In FIG. 14, a graph 64 shows an acceleration Ax in the X-direction, an acceleration Ay in the Y-direction and an acceleration Az in the Z-direction measured by the acceleration sensors included in the motion sensor 56 provided to near the sacral bone, the horizon axis indicates "time (sec.)" and the vertical axis indicates "accelerations (m/sec.$^2$)".

A graph 65 shows an angular speed Wx in the X-direction, an angular speed Wy in the Y-direction and an angular speed Wz in the Z-direction measured by the angular speed sensors included in the motion sensor 56 provided to near the sacral bone, the horizon axis indicates "time (sec.)" and the vertical axis indicates "angular speed (rad/sec.$^2$)".

A graph 66 shows an acceleration Ax in the X-direction, an acceleration Ay in the Y-direction and an acceleration Az in the Z-direction measured by the acceleration sensors included in the motion sensor 58 provided to near the sixth thoracic vertebrae, the horizon axis indicates "time (sec.)" and the vertical axis indicates "accelerations (m/sec.$^2$)".

A graph 67 shows an angular speed Wx in the X-direction, an angular speed Wy in the Y-direction and an angular speed Wz in the Z-direction measured by the angular speed sensors included in the motion sensor 58 provided to near the sixth thoracic vertebrae, the horizon axis indicates "time (sec.)" and the vertical axis indicates "angular speed (rad/sec.$^2$)".

In FIG. 14, a setting part 68 for setting a measuring timer period is provided on the right side of the graphs. An indicating part 69 for indicating a remaining period of measurement is provided under the setting part 68. Further, a start/stop button 70 for starting or stopping the measurement is provided.

Note that, as to the data shown in FIG. 14, the data being measured can be displayed in real time, and the data which have been previously measured can be displayed, too. In case of storing the measured data (the data previously measured and stored), the measured data can be read and the graphs 64-67 can be displayed by pushing a stored data button 71.

Figure 15:
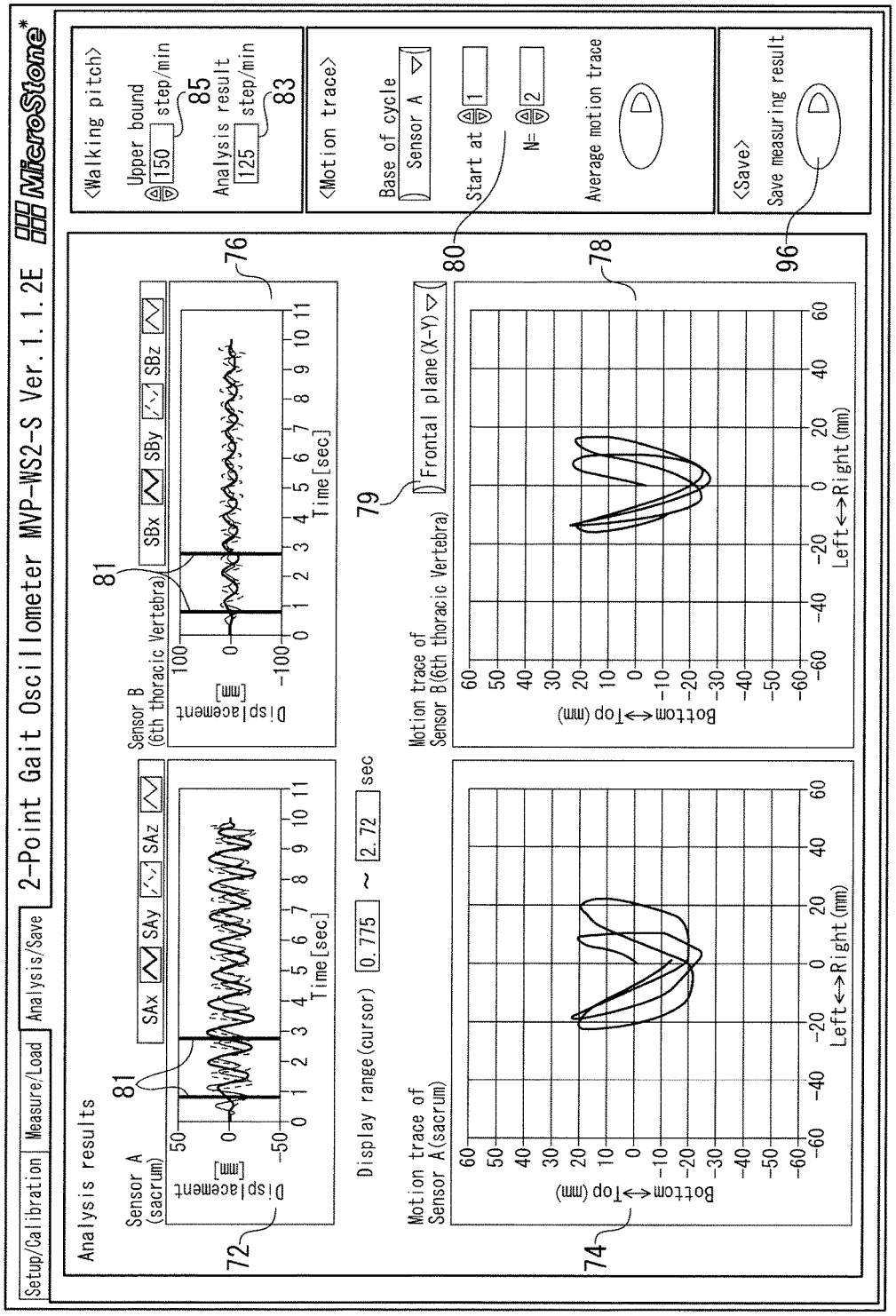
FIG. 15 is an explanation view of a screen for analyzing data from each of the motion sensors and showing the analyzed data, which is displayed by the detecting device of the fourth embodiment.

FIG. 15 shows a screen displaying the results of analyzing the data shown in FIG. 14.

The calculating means 34 removes low frequency components from the accelerations Ax in the X-direction, the accelerations Ay in the Y-direction and the accelerations Az in the Z-direction by the high-pass filter. The integrator 37 of the calculating means 34 integrates the rocking accelerations, which have been extracted in the filtering process, once to calculate rocking speeds and integrates the same twice to calculate rocking amounts.

A graph 72 in an upper-left part of FIG. 15 shows displacements of the motion sensor 56 provided to near the sacral bone in the X-, Y- and Z-directions respectively. The horizontal axis of the graph 72 indicates "displacement (mm)", and the vertical axis thereof indicates "time (sec.)".

In the graph 72, the displacements in the three directions indicated by the vertical axis are distances from a reference stop position (0).

A graph 74 in a lower-left part of FIG. 15 shows Lissajous figures of the displacement of the motion sensor provided to near the sacral bone, the vertical axis indicates "displacement (mm)" in the vertical direction, and the horizontal axis indicates "displacement (mm)" in the left/right direction.

A graph 76 in an upper-right part of FIG. 15 shows Lissajous figures of the displacement of the motion sensor 58 provided to near sixth thoracic vertebrae in the X-, Y- and Z-directions respectively, the vertical axis indicates "displacement (mm)" in the vertical direction, and the horizontal axis indicates "displacement (mm)" in the left/right direction. The horizontal axis of the graph 76 indicates "displacement (mm)", and the vertical axis thereof indicates "time (sec.)".

In the graph 76, the displacements in the three directions indicated by the vertical axis are distances from the reference stop position (0).

A graph 76 in a lower-right part of FIG. 15 shows Lissajous figures of the displacement of the motion sensor 58 provided to near sixth thoracic vertebrae, the vertical axis indicates "displacement (mm)" in the vertical direction, and the horizontal axis indicates "displacement (mm)" in the left/right direction.

As to the track graphs 74 and 78 of FIG. 15 showing the Lissajous figures, the graphs in the X-Y plane, Y-Z plane of X-Z plane can be selectively displayed by pushing a select button 79. In FIG. 15, the X-Y plane is displayed as a frontal plane, and the Y-Z plane a saggital plane or the X-Z plane (the horizontal plane) can be further displayed by pushing the select button 79.

As to the displayed data of the track graphs 74 and 78 shown in FIG. 15, a walking cycle of a selected time period to be displayed can be optionally selected from walking cycles which have been actually measured. Selecting the walking cycle can be performed in a select screen 80. In FIG. 15, a first walking and a second walking cycle are displayed, but it is preferable to select a middle part of the cycles during stable walking. The range of the walking cycle selected in the select screen 80 is displayed by two thick lines 81 in the graphs 72 and 76 showing the displacements of the motion sensors 56 and 58.

The calculating means 34 is capable of calculating a walking pitch on the basis of the rocking amounts, which have been obtained from the data measured by the motion sensors 56 and 58. One walking pitch is from putting one foot on the ground to nextly putting the same foot on the ground.

The calculated walking pitch is displayed in an extraction window 83. Further, the calculating means 34 is capable of calculating the walking pitch within a maximum limit, which can be set, by the operator, in a maximum limit setting window 85.

The measured data of the graphs shown in FIG. 15 and analyzing conditions can be stored in the storing device 44 by pushing a storing button 96.

The measured data and the analyzing conditions can be store as, for example, CSV files.

Figure 16:
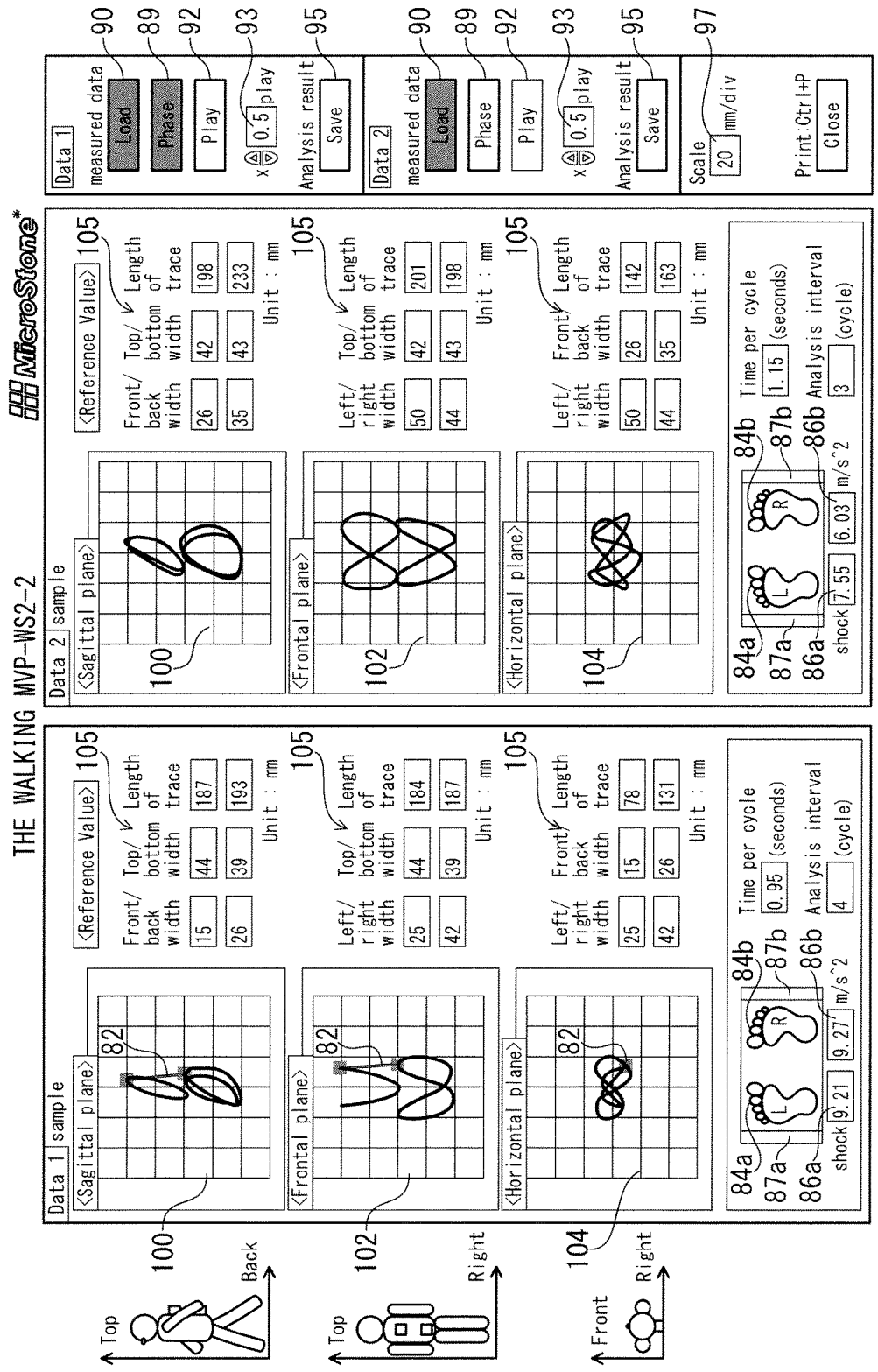
FIG. 16 is an explanation view of a screen showing comparison results of the analyzed data shown in FIG. 15, which is displayed by the detecting device of the fourth embodiment.

The displaying means finally makes a screen shown in FIG. 16, which will be provided to the subject.

FIG. 16 is characterized in that the Lissajous figures of the displacements of the places near the sacral bone and near the sixth thoracic vertebrae, which are detected by the motion sensors 56 and 58, in the Y-A plane the saggital plane 100, the X-Y plane (the frontal plane) and the X-Z plane (the horizontal plane) are simultaneously displayed.

Note that, in FIG. 16, the three Lissajous figures correspond to the two kinds of data are disposed on right and left to compare with each other, but the figures correspond to one kind of the two may be displayed.

The displaying means 36 is capable of displaying connection lines 82, each of which connects same time points in the Lissajous figures of the motion sensors 56 and of said two places to each other, and moves the connection lines 82 with the lapse of time.

When the operator pushes a phase button 89 which is located in the right part of the screen, the displaying means 36 displays the connection lines 82. A playback button 92 is provided under the phase button 89. By pushing the playback button 92, the displaying means 36 displays and moves the connection lines with the lapse of time. A playback speed of displaying the connection lines 82 can be changed by changing a number in a playback speed window 93. When the number in the playback speed window 93 is 1.0, the playback is performed in a normal time; when the number therein is 0.5, the playback can be performed in a half of the normal time.

Indication parts 105, in each of which rocking widths and track lengths of each Lissajous figure are indicated, are respectively disposed adjacent to the Lissajous figures of the Y-Z plane the saggital plane 100, the X-Y plane (the frontal plane) 102 and the X-Z plane (the horizontal plane) 104.

The displaying means 36 calculates front-to-rear widths (mm), vertical widths (mm) and track lengths (mm) relating to the Y-Z plane the saggital plane 100 and displays them in the indication parts 105.

The displaying means 36 calculates left and right widths (mm), vertical widths (mm) and track lengths (mm) relating to the X-Y plane (the frontal plane) 102 and displays them in the indication parts 105.

The displaying means 36 calculates left and right widths (mm), front-to-rear widths (mm) and track lengths (mm) relating to the X-Z plane (the horizontal plane) 104 and displays them in the indication parts 105.

Images of soles 84*a* and 84*b* of the left foot and the right foot are shown under the Lissajous figures, and impact values applied to specified places in the soles are displayed in impact value windows 86*a* and 86*b*. Instruction bars 87*a* and 87*b*, which are used to optionally specify the places in the soles, are located near the images of the soles 84*a* and 84*b*, and the operator can optionally specify the places in the soles by operating the instruction bars 87*a* and 87*b*.

When the operator operates the instruction bars 87*a* and 87*b*, the calculating means 34 calculates vertical accelerations in the specified places detected by the motion sensor 56, and the displaying means 36 displays the calculated accelerations in the impact value windows 86*a* and 86*b* as the impact values.

Note that, in case that a rearmost part of the Lissajous figure (formed like "∞") of the X-Z plane (the horizontal plane) relating to the motion sensor 56 is regarded as a time point when a heal contacts the ground and that a frontmost part thereof is regarded as a time point when a toe leaves the ground, the places in each of the soles can be known.

The analysis results shown in FIG. 16 can be stored in the storing device 44 by pushing a storing button 95. The analysis results can be store as, for example, a CSV file.

Further, scales of the Lissajous figures can be changed by changing a number displayed in a scale window 97.

Note that, the displaying means 36 is capable of making video images (animations) of three dimensional movement of the subject on the basis of the displacements of the place near the sacral bone and the place near sixth thoracic vertebrae in the Y-Z plane the saggital plane, the X-Y plane (the frontal plane) and the X-Z plane (the horizontal plane) detected by the motion sensors 56 and 58.

Note that, in each of the former embodiments too, the places of the motion sensors may be measured, and Lissajous figures may be corrected on the basis of the positional relationship between the motion sensors.

For example, the subject is compulsorily taken a reference position when the subject is in a stationary state. To take the reference position, an assistant may correct the posture or a posture correcting member may be attached to the subject. Then, the subject is made relax and made take an easy posture. In this action, a rocking amount from the reference posture to an original posture or ordinary posture of the subject (physical feature) is calculated by the calculating means 34. Namely, positional displacement, inclination and twist between the motion sensors of the lumber area and the thoracodorsal area can be known. For example, in case that a right shoulder of the subject is originally lowered, the motion sensor of the thoracodorsal area is inclined rightward more than the motion sensor of the lumber area; in case that the subject is round-shouldered, the motion sensor of the thoracodorsal area is inclined forward more than the motion sensor of the lumber area.

For example, when it is known that the motion sensor of the thoracodorsal area is rightwardly shifted 1 cm from the motion sensor of the lumber area on the basis of the rocking amounts calculated by the calculating means 34, the displaying means 36 corrects to rightwardly shift the Lissajous figure of the rocking amount of the thoracodorsal area 1 cm.

By this action, the original physical features can be confirmed, from the Lissajous figures, even in the walking state.

The Lissajous figures may be displayed with considering physical features of the subject while walking, not physical features of the stationary state. Some subjects can take the reference postures, but they will sometimes take bad postures or good postures while walking.

In such case, the calculating means 34 calculates positional displacements of the motion sensors attached to the walking subject, in orthogonal coordinate systems, so as to calculate physical features of the subject while walking.

Then, the displaying means 36 corrects the Lissajous figures of the rocking amounts on the basis of the physical features. With this manner, the physical features while walking too can be confirmed.

Fifth Embodiment

Figure 17:
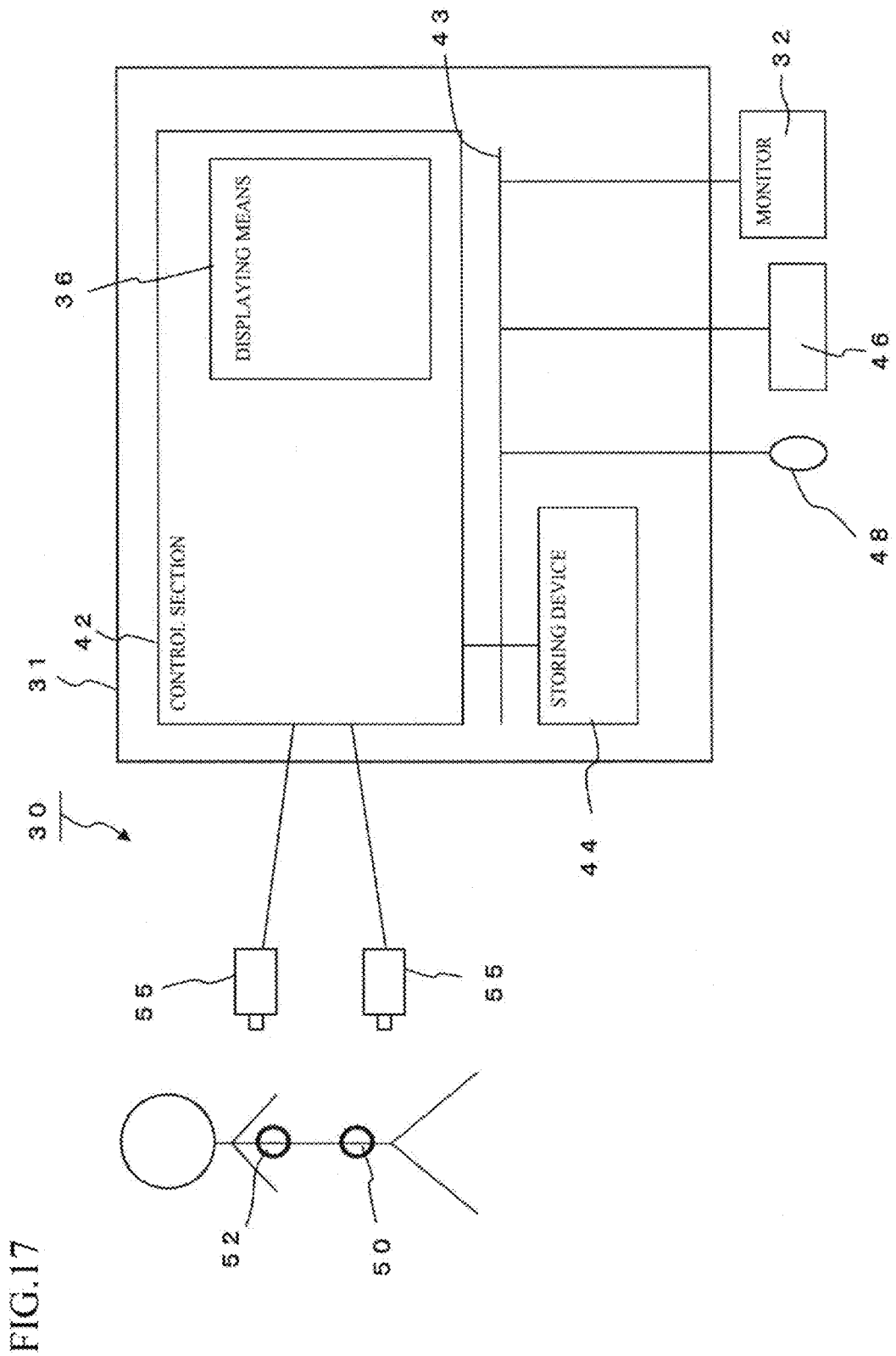
FIG. 17 is an explanation view of a fifth embodiment of the device for detecting an ambulatory status.

An embodiment, in which conditions of movement are measured on the basis of images photographed by high speed cameras without using motion sensors, will be explained with reference to FIG. 17.

Note that, the structural elements described in the former embodiments are assigned the same symbols and explanation will be omitted.

High speed cameras 55 are publicly known cameras which are capable of photographing several dozens of frames a second. A plurality of the high speed cameras 55, which are disposed at different positions, are provided so as to improve a measuring accuracy.

Markers 50 and 52 are respectively attached in the lumber area 12 and the thoracodorsal area 14. The high speed cameras 55 photograph the markers 50 and 52.

Photographed image data are inputted to the main device section 31.

In the main device section 31, the displaying means realized by the control section 42 displays the conditions of movement of the markers 50 and 52, on the basis of the image data, on the monitor 32. At this time, the image data photographed by the high speed cameras 55 located at different positions are inputted to the main device section 31, so it is preferable to display three dimensional movements of the markers 50 and 52, i.e., moving tracks of the markers 50 and 52 (not shown).

Note that, in the present embodiment, the motion sensors described in the former embodiments may be provided to the places of the markers 50 and 52, and means for calculating conditions of movement of said two places on the basis of data measured by the motion sensors may be further provided (not shown).

In this case, the displaying means 36 superposes the moving tracks of the markers 50 and 52, which have been photographed by the high speed cameras 55, and displays the superposed tracks on the monitor 32, further the displaying means can superpose the conditions of movement of said two places and can display the superposed conditions on the monitor 32.

Further, a positional relationship between the motion sensors attached to the subject in the stationary state may be measured by using the high speed cameras 55. The positional relationship between the motion sensors are, for example, positional displacement, inclination and twist between the motion sensors of the lumber area and the thoracodorsal area. For example, in case that a right shoulder of the subject is originally lowered, the motion sensor of the thoracodorsal area is inclined rightward more than the motion sensor of the lumber area; in case that the subject is round-shouldered, the motion sensor of the thoracodorsal area is inclined forward more than the motion sensor of the lumber area.

By photographing the positions of the motion sensors of the subject being stationary with the high speed cameras 55, the above described positional relationships can be known. The displaying means 36 is capable of correcting the Lissajous figures of the rocking amounts measured by the motion sensors on the basis of the positional relationship between the motion sensors and displaying the corrected figures on the monitor 32. For example, when it is known that the motion sensor of the thoracodorsal area is rightwardly shifted 1 cm from the motion sensor of the lumber area on the basis of the rocking amounts calculated by the calculating means 34, the displaying means 36 corrects to rightwardly shift the Lissajous figure of the rocking amount of the thoracodorsal area 1 cm.

By this action, the original physical features of the subject can be confirmed, from the Lissajous figures, even in the walking state.

In the above described embodiments, the conditions of movement of the subject 10 are measured in the two places, i.e., the lumber area 12 and the thoracodorsal area 14, but the conditions of movement may be measured in three places or more, e.g., head.

Note that, in the above described embodiments, the motion sensors are the acceleration sensors only, the angular speed sensors only or the magnetic sensors only, but a combination or combinations of the acceleration sensor, the angular speed sensor and the magnetic sensor may be employed.

In such case, a combination or combinations of accelerations, speeds, positions, angular speeds and angles can be measured.

In each of the above described embodiments, a large-sizes monitor may be employed as the monitor 32, and the subject may walk with watching his own posture displayed on the monitor.

In this case, the subject can walk with correcting his posture, so a feedback effect can be obtained.

Further, the displaying means 36 is capable of making personified images, e.g., computer graphics, animations, on the basis of the analysis results of Lissajous figures, and the displaying means may display the personified images on the monitor 32. With this manner, the subject can easily understand the analysis results.

(Use of Device for Detecting Ambulatory Status)

The conditions of movement of the lumber area and the thoracodorsal area can be known by the above described device for detecting the ambulatory status, so effects of an insole of a shoe can be confirmed.

These days, manufacturers have developed insoles of many kinds of shoes, e.g., running shoes, climbing shoes, winter sports shoes, and the insoles are composed of suitable materials and formed into suitable shapes on the basis of uses.

In FIG. 16, the two kinds of data are displayed on right and left, and the data can be changed by pushing a read button 90. Therefore, by attaching no insoles to shoes, attaching insoles to the shoes and changing insoles, the operator can collect a plurality of sets of data of the motion sensors and display the two kinds of data under different conditions on the monitor 32.

By displaying the data collected under different conditions on one screen as shown in FIG. 16, the ambulatory statuses under different conditions can be easily known.

As to the example shown in FIG. 16, Data 2 on the right side indicate existence of walking deviations in the three directions, i.e., forth/back direction, left/right direction and vertical direction; on the other hand, Data 1 on the left side indicate the good ambulatory state.

Conventionally, effects of insoles, e.g., walking ease, are subjectively judged by a subject only, but the effects can be easily objectively judged by the device for detecting an ambulatory status.

(Other Uses of Device)

The device for detecting an ambulatory status can be used for not only confirming effects of insoles but also confirming whether shoes are good or bad. By changing shoes, the operator can collect data of the motion sensors a plurality of times, so that suitable shoes capable of producing a good ambulatory status can be easily objectively judged.

Further, the device for detecting ambulatory status is capable of confirming effects of rehabilitation. By collecting data of the motion sensors before and after performing rehabilitation, the operator can easily objectively judge whether the rehabilitation improves the ambulatory status or not.

The device for detecting ambulatory status is capable of confirming effects of physical training and stretching exercise. By collecting data of the motion sensors before and after performing physical training or stretching exercise, the operator can easily objectively judge whether the physical training or stretching exercise effectively improves the ambulatory status or not.

The preferred embodiments of the present have been explained above, but the present invention is not limited to the embodiments and many modifications can be allowed without deviating from the scope of the invention.

What is claimed is:

1. A device for detecting an ambulatory status, comprising:
    a monitor;
    motion sensors being respectively provided to a lumbar area and a thoracodorsal area;
    means for calculating conditions of movement in said lumbar area and thoracodorsal area on the basis of data measured by the motion sensors; and
    means for superposing the conditions of movement in said lumbar area and thoracodorsal area, which have been calculated by the calculating means, and displaying the superposed conditions on the monitor,
    wherein each of the motion sensors is any selected from an acceleration sensor, an angular speed sensor, or a combination thereof,
    wherein the calculating means extracts only vibration components by filtering the data detected by the motion sensors, and the extracted vibration components are integrated so as to calculate any of rocking accelerations, rocking speeds and rocking amounts,
    wherein the displaying means makes Lissajous figures of said lumbar area and thoracodorsal area, in a horizontal plane, on the basis of any of rocking accelerations, rocking speeds and rocking amounts calculated by the calculating means, superposes the Lissajous figures of said lumbar area and thoracodorsal area and displays the superposed figures on the monitor, and
    wherein the displaying means displays a connection line, which connects same time points in the Lissajous figures of the motion sensors of said lumbar area and thoracodorsal area to each other, and moves the connection line with a lapse of time.

* * * * *